United States Patent [19]

Lewis et al.

[11] 4,002,637
[45] Jan. 11, 1977

[54] OXAZOLIDINE, OXAZOLIDINE-CONTAINING CONDENSATION AND ADDITION POLYMERS AND METHODS OF PRODUCING THEM

[75] Inventors: Sheldon N. Lewis, Zurich, Switzerland; Jerome F. Levy, Dresher; Napoleon L. Horton, Philadelphia, both of Pa.

[73] Assignee: Rohm and Haas Company, Philadelphia, Pa.

[22] Filed: Jan. 10, 1975

[21] Appl. No.: 540,021

Related U.S. Application Data

[63] Continuation-in-part of Ser. Nos. 377,375, July 9, 1973, abandoned, and Ser. No. 377,377, July 9, 1973, Pat. No. 3,937,716.

[52] U.S. Cl. .................. 260/307 FA; 260/33.6 R; 260/75 N; 260/33.6 UA
[51] Int. Cl.² ........................................ C07D 263/02
[58] Field of Search ............ 260/307 FA, 377, 375

[56] References Cited
OTHER PUBLICATIONS

Gaylord, "Polyethers," Interscience, pp. 200–205, (1963).

*Primary Examiner*—Donald G. Daus
*Assistant Examiner*—D. B. Springer

[57] ABSTRACT

The present invention is concerned with novel oxazolidines, polyoxazolidines, and particularly polymers of both condensation and addition type containing 1,3-oxazolidine groups linked to the polymer through an aliphatic ester linkage. They are the products of reaction between (1) 3-glycidyl-1,3-oxazolidines which may be substituted in the 2-position with an alkyl or aralkyl group and (2) a monocarboxylic acid, a polycarboxylic acid, or a polymer (of addition or condensation type) containing at least one carboxyl group. The polymeric products have improved adhesion when employed as adhesive or coating materials. The oxazolidine in such polymeric substances improves the usefulness of the polymers in regard to adhesiveness or cohesiveness when such polymers are used as coating compositions, adhesive compositions and for the molding of plastic articles. The non-polymeric products serve as intermediates which can be used as reactive components to react with carboxyl groups of addition or condensation polymers to introduce oxazolidine groups into such polymers to modify their adhesiveness. This application also covers methods of producing the new oxazolidine products and moisture-curable mixtures of a polyisocyanate and a reaction product of (1) and (2) above.

12 Claims, No Drawings

OXAZOLIDINE, OXAZOLIDINE-CONTAINING CONDENSATION AND ADDITION POLYMERS AND METHODS OF PRODUCING THEM

This application is a continuation-in-part of our earlier copending applications, Ser. Nos. 377,375, filed July 9, 1973, and now abandoned; and 377,377, filed July 9, 1973, now U.S. Pat. No. 3,937,716, issued Feb. 10, 1976.

DESCRIPTION OF THE INVENTION

The earlier applications mentioned disclose the preparation of new 3-(glycidyl)-1,3-oxazolidines of the formula

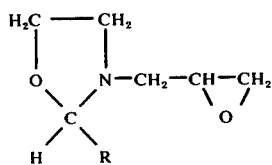

(the ring of which may be stylized as follows:

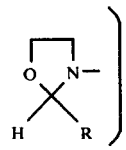

wherein R is selected from the group consisting of H, alkyl or aralkyl, especially lower alkyl of 1 to 8 carbon atoms and benzyl. Specific examples of alkyl group include methyl, ethyl, n-propyl, isopropyl, n-butyl, sec-butyl, tert.-butyl, hexyl, and 2-ethylhexyl. In preferred instances R is an alkyl group having 1 to 4 carbon atoms. These new glycidyl oxazolidines are valuable intermediates which react (and thereby combine) with carboxylic acids and particularly carboxylic acid polymers to produce novel polymeric oxazolidines which can be used in coating compositions which have excellent adhesiveness to various substrates, such as wood and metals, primed, previously painted, or unprimed or unpainted.

Examples of polycarboxylic acids that may be reacted with the compounds of formula I include such dicarboxylic acids as oxalic, succinic, adipic, azelaic, sebacic and phthalic. The relative proportions between the diacid and the oxazolidine of formula I may be such as to esterify both the carboxyl groups, one only, or provide a mixed product of mono- and di-ester. Additional polycarboxylic acids that can be reacted with the glycidyl oxazolidines of formula I include trimesic, tricarballylic, citric, and tartaric. Again, if desired, only one of the carboxyl groups may be esterified, thus providing a polycarboxylic acid (especially a dicarboxylic acid), containing an oxazolidine group which can be included with other polycarboxylic acids, especially one or more of the dicarboxylic acids, such as adipic, maleic, phthalic, etc., mentioned above in the production of condensation polyesters, such as alkyds, using therewith polyhydric alcohols, such as ethylene glycol, propylene glycol, glycerol, pentaerythritol, etc. Such polyesters would contain oxazolidine groups and would not need post-reaction with the compounds of formula I herein to introduce the oxazolidine groups therein.

The compounds of formula I react with monocarboxylic acids to produce esters containing an oxazolidine group. This is particularly advantageous in the case of monoethylenically unsaturated acids, such as acrylic, methacrylic, itaconic, citraconic, aconitic, crotonic, and α-chloroacrylic, thereby producing addition-polymerizable monomeric esters which contain an oxazolidine nucleus. Such esters may be homopolymerized, but are preferably copolymerized with one or more other monoethylenically unsaturated monomers, such as methyl acrylate or methacrylate, ethyl acrylate or methacrylate, butylacrylate or methacrylate, styrene, acrylonitrile, vinylidene chloride, acrylic acid, methacrylic acid, itaconic acid, vinyl acetate, hydroxyethyl acrylate or methacrylate, acrylamide, methacrylamide, N-methylol-acrylamide or -methacrylamide, ethylene, etc. Similarly, an addition-polymerizable monomer containing the oxazolidine group is obtained by reacting the glycidyl oxazolidine of formula I with maleic acid or fumaric acid.

The glycidyl oxazolidines of formula I produce particularly valuable products by the reaction thereof with condensation polymers and particularly polyesters having terminal carboxyl groups and having molecular weights from about 500 to 12,000. The products obtained have improved adhesion when they are employed as coating compositions or components of coating compositions. Similarly, they show improved qualities in respect to internal cohesion when used in the making of molded or otherwise formed plastic articles.

The 3-(glycidyl)-1,3-oxazolidines (I) provide an excellent means for incorporating the oxazolidine moiety into carboxylic acid-containing addition polymers and condensation polyesters via post-reaction of said polymers and polyesters with an oxirane moiety of the 3-(glycidyl)-1,3-oxazolidine (I). This approach, applied to acid-terminated polyesters is especially attractive for the preparation of polyoxazolidines sufficiently low in molecular weight (500–2500) to be of interest in low solvent, high concentration formulations. Reactive blends of polyoxazolidines thereby obtained with polyisocyanates and polyanhydrides are of considerable interest in a variety of applications including industrial coatings, leather finishes and adhesives. Such blends are moisture-curable.

The 3-(glycidyl)-1,3-oxazolidines (I) react with monocarboxylic acids and polycarboxylic acids including bis-carboxylic acids and polymeric acids in non-aqueous systems to produce oxazolidine-containing esters or polyoxazolidines (III). The relative stability of those 3-(glycidyl)-1,3-oxazolidines (I) wherein R is a hydrocarbyl radical of aliphatic type (alkyl or aralkyl) makes it possible to condense same with carboxylic acids at elevated temperatures of from about 80° to about 85° C. over a period of several hours. In general, the proportion of 3-(glycidyl)-1,3-oxazolidine (I) carboxylic acid is not critical to the process. Stoichiometric mixtures consistently resulted in yields of 65–70% conversion to ester product but an excess of 3-(glycidyl)-1,3-oxazolidine (I) generally resulted in an increase in the yield of product. The following equation illustrates this process:

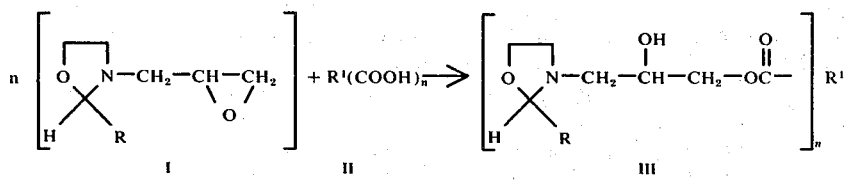

wherein $R^1$ may be a covalent bond as in oxalic acid, the radical or residual portion of a monocarboxylic acid attached to the carboxylic group, an alkylene chain of 2–10 carbon atoms, an alkenylene chain of 2–10 carbon atoms, arylene, for example, a mononuclear arylene such as phenylene, or an alkenyl group of 2–10 carbon atoms, and $n$ is an integer having a value of 1 or 2. Thus, $R^1(COOH)_n$ may be a mono- or polycarboxylic acid containing from 2–10 carbon atoms and R is a hydrocarbyl group as defined above. Preferably, $R^1$ is a polymeric residue of an addition or condensation polymer containing carboxyl groups in which case $n$ may be 2 to 100 or 1000. The reaction is effected by simply mixing the reactants, either directly or in an inert solvent, and applying heat. The use of a catalyst in the process is purely optional but tetraalkylammonium salts, such as benzyltrimethylammonium halide, or tertiary amines, such as triethylamine, are preferred. When stoichiometric amounts of the reactants are employed there is a conversion of approximately 65–70% of the available acid functionality to oxazolidine. A side reaction such as polymerization, oligomerization or rearrangement of the glycidyloxazolidine takes place in completion with the desired addition to the carboxy group and this accounts for the moderate degree of conversion. Higher conversions of up 90% can be achieved by employing excess glycidyloxazolidine.

The polyoxazolidines (III) obtained via the foregoing process have many industrial uses, but, as a practical matter, their actual application may be hindered by interference from residual unconverted carboxylic acid. However, this drawback may be eliminated by the post-reaction of said acid with another epoxide (IV) such as ethylene oxide or propylene oxide.

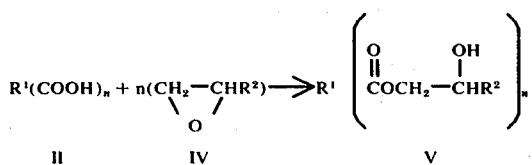

wherein $R^1$ is as defined above and $R^2$ is hydrogen or methyl. In this manner any residual acid is effectively eliminated via conversion to a product which is compatible with the ester-containing oxazolidine product (V).

The polyoxazolidines (III) are particularly valuable in terms of room temperature cure with isocyanate and anhydride pre-polymers under conditions where a mixture is available to produce plastics, coatings and adhesives with outstanding mechanical properties. The exposure of a freshly prepared mixture of aliphatic diisocyanate, e.g., 4,4'-methylene-bis(cyclohexylisocyanate) with a polyoxazolidine (III) at 25° C. results in a system which has a short gel time but the exposure of freshlymixed systems to ambient conditions (≈23° C., 40% relative humidity) generally produces films which are tack-free within 2–3 hours and which are hard, clear and abrasion-resistant within 24 hours. In several initial screening tests diisocyanate/polyoxazolidine mixtures provided significant improvements in leather properties when used as solvent impregnants. In addition, an improvement in early and cured peel strength in fabric bonding application was also observed.

The reaction between the polyoxazolidines (III) and polyisocyanates is initiated by the presence of moisture. Atmospheric moisture is generally sufficient to initiate the polymerization and effect a cure of the composition. Also, if desired, water may be added to the compositions to effect the cure. It is believed that the polymeric products may be the result of a rapid hydrolysis of the polyoxazolidines (III) in which the oxazolidine ring is opened and an amino alcohol is formed. The amino alcohol may then react with the polyisocyanate at either the active hydrogen of the amino group or the active hydrogen of the hydroxy group but it is believed that the reaction at the amino nitrogen may occur more readily. This process, namely, hydrolysis of the oxazolidine ring and subsequent reaction with a polyisocyanate, generally occurs quite rapidly at ambient temperatures but elevated temperatures may be used if desired.

The ratio of polyisocyanate to polyoxazolidine (III) is not critical and can vary over a wide range to influence the nature and property of the desired polymeric product. For example, the polyisocyanate and polyoxazolidine can be present in ratios such that the reaction during cure will take place primarily between the polyisocyanate and the amino group of the hydrolyzed polyoxazolidine. In general, the ratio of polyisocyanate to polyoxazolidine (III) is from about 1:10 to 100:1 molecular equivalents with the preferred ratio being from about 1:1.1 to about 2.5:1. Also, the reaction can be carried out with or without the use of a catalyst. Suitable catalysts include, for example, acids such as p-toluene sulfonic acid, dibutyltin octoate, zinc chloride, hydrogen chloride or the like. The catalysts are generally employed in an amount of from about 0.001% to about 10% by weight based on the weight of polyoxazolidine and, preferably, from about 0.1% to about 5% by weight. The curing may be conducted with or without the use of a solvent but, since the rate of hydrolysis of the polyoxazolidine and the subsequent curing with polyisocyanate can be influenced by the presence of such media, solvents are generally employed. Especially preferred solvents are those which are substantially free from active hydrogen as determined by the Zerewitinoff method described in Kohler et al (Journal of the American Chemical Society, Volume 40; pages 2181–2188; 1927) and should be substantially anhydrous. Typical of these solvents are, for example, toluene, xylene, aliphatic hydrocarbons, isopropyl ether, ethyl acetate, beta-ethoxyethyl acetate, methyl ethyl ketone and the like and mixtures thereof. Pigments, dyes, fillers, antiozodants, antioxidants, stabilizers, flow-control agents or other optional ingredients can also be included in the composition.

Typical of the diisocyanates which may be combined with the polymeric oxazolidines (III) of this invention are the following: saturated aliphatic and cycloaliphatic diisocyanates, unsaturated aliphatic and cycloaliphatic diisocyanates, aromatic and polyaromatic diisocyanates, isocyanates derived from aliphatic polyamines, carbonate-containing diisocyanates, di-alkyl ether-containing diisocyanates, vinyl polymers containing isocyanato-ethyl methacrylate as a monomer or comonomer and prepolymers of polyisocyanates with polyhydroxy-or polyamino-substituted alkanes and cycloalkanes. Examples of the foregoing diisocyanates include: 1,6-hexamethylene diisocyanate, 1,8-octamethylene diisocyanate, 1,12-dodecamethylene diisocyanate, 2,2,4-trimethylhexamethylene diisocyanate, 3,3'-diisocyanatodipropyl ether, 3-isocyanatomethyl-3,5,5-trimethylcyclohexylisocyanate, cyclopentylene-1,3-diisocyanate, cyclohexylene-1,4-diisocyanate, methyl 2,6-diisocyanatocaproate, bis-(2-isocyanatoethyl)fumarate, 4-methyl-1, 3-diisocyanatocyclohexane, trans-vinylene diisocyanate, 4,4'-methylene-bis-(iso-cyanatocyclohexane)methane diisocyanate, N,N',N''-(6-isocyanatohexamethylene) biuret, bis-(2-isocyanatoethyl) carbonate, tolylene diisocyanates, xylylene diisocyanates, dianisidine diisocyanate, 4,4'-diphenylmethane diisocyanate, 1-ethoxy-2,4-diisocyanatobenzene, 1-chloro-2,4-diisocyanatobenzene, tris-(4-isocyanatophenyl) methane, naphthalene diisocyanates, fluorene diisocyanates, 4,4'-biphenyl diisocyanate, phenylene diisocyanates, 3,3'-dimethyl-4,4' biphenyl diisocyanate, p-isocyanatobenzyl isocyanate, tetrachloro-1,3-phenylene diisocyanate, 2,4,6-tribromo-1,3-phenylene diisocyanate, bis(2-isocyanatoethyl) benzene, 3-isocyanatomethyl-3,3,5-trimethylcyclohexylisocyanate, tolylene diisocyanate, menthane diisocyanate, 4,4'-methylene-bis-(cyclohexylisocyanate), 4,4'-methylene-bis-(isocyanatocyclohexane) and 2-isocyanatoethyl-6-isocyanatocaproate.

The isocyanate prepolymers of the preceding paragraph are prepared by methods well-known to those skilled in the art. Generally, the preparation of the prepolymers involves the reaction of a polyol, polyether, hydroxylterminated polyester, polyester amide, or other polyfunctional active hydrogen compound with a diisocyanate or other polyisocyanate, preferably, using an excess of the isocyanate to yield an isocyanate-terminated prepolymer product. An extensive description of some of the useful techniques for preparing the isocyanate prepolymers can be found in the text entitled: J. H. Saunders and K. C. Frisch, *Polyurethanes: Chemistry and Technology*, Part II, Interscience, (New York); pages 8–49 (1964).

Other polyfunctional isocyanates which can be combined with the polymeric oxazolidines (III) of this invention are those disclosed in U.S. Pat. No. 3,162,664, of Brotherton et al., granted Dec. 22, 1964; U.S. Pat. No. 3,427,346, of Brotherton et al., granted Feb. 11, 1969; U.S. Pat. No. 3,275,679, of Brotherton et al., granted Sept. 27, 1966; U.S. Pat. No. 3,352,830, 1967; U.S. Pat. No. 2,729,666 of Stallmann, granted Jan. 3, 1956; U.S. Pat. No. 2,768,154 of Unruh et al., granted Oct. 23, 1956; U.S. Pat. No. 3,267,122 of Lehmann et al., granted Aug. 16, 1966; U.S. Pat. No. 3,281,378, of Garber et al., granted Oct. 25, 1966; U.S. Pat. No. 3,124,605, of Wagner, granted Mar. 10, 1964; U.S. Pat. No. 2,718,516 of Bortnick, granted Sept. 20, 1955; as well as isocyanates prepared from the amines disclosed in U.S. Pat. No. 3,256,318 of Brotherton et al., granted June 14, 1966.

The polymeric products obtained via the condensation of the polymeric oxazolidines (III) with polyisocyanates have utility in forming films, fibers, paints, lacquers, varnishes, seamless caulks, coatings and impregnants and as adhesives for both natural and synthetic materials such as paper, textiles, wood, plastics, metal and leather and as binders for non-woven fabrics. To prepare coatings and films, the polymeric product can be applied with or without a solvent by casting permanently or removably onto a suitable substrate.

The Examples which follow illustrate the products of this invention and the methods by which they are obtained. However, the examples are illustrative only and it will be apparent to those having ordinary skill in the art that this invention includes functionally equivalent products and methods for their preparation. Therefore, any modification of the claimed syntheses which result in the formation of an identical product should be construed as constituting an analogous method. The claimed processes are capable of wide variation and modification and, therefore, any minor departure therefrom or extension thereof is considered as being within the skill of the artisan and within the scope of this invention.

EXAMPLE A 3-(Glycidyl)-2-Isopropyl-1,3-Oxazolidine

Step A: 2-Isopropyl-1,3-Oxazolidine

Into a 2 liter, three-necked flask equipped with a bottom stopcock, mechanical stirrer, thermometer and dropping funnel there are charged 305 g. (5.0 moles) ethanolamine, 35 g. (0.25 moles) anhydrous potassium carbonate and 450 cc. of toluene. To the stirred mixture is added 360 g. (5 moles) of isobutyraldehyde via a dropping funnel over a 20 minute period while the temperature rises to a maximum of 67° C. The dropping funnel is replaced with a Dean-Stark trap and the solution is stirred and allowed to cool to room temperature. The stirrer is stopped and separation of the organic and aqueous phases is allowed to occur over an approximately 15 minute period. The bottom aqueous layer is removed via the bottom stopcock and the remaining solution is heated to reflux at reduced pressure (180 mm. Hg) and the water-toluene azeotrope is collected (50 ml. water). The solution is stripped by gradually reducing the pressure to 20 mm. Hg., and continued until distillation ceases at the solution temperature of 55° C. The resulting 2-isopropyloxazolidine (552 g., 96% yield) is a clear, colorless, mobile liquid.

Analysis for $C_6H_{13}NO$: Calculated: %C, 62.49; %H, 11.39; %N, 12.15. Found: %CC, 61.09; %H, 11.17; %N, 11.35. Neutralization Equivalent ($HClO_4$) Found: 112.9; Theoret.: 115.17. GLC Analysis 98 + % purity.

Step B: 3-(3-Chloro-2-hydroxypropyl)-2-Isopropyl-1,3-Oxazolidine

Into a 2 liter, three-necked flask equipped with a mechanical stirrer, thermometer and a dropping funnel there is charged 515 g. (5.0 moles) of crude 2-isopropyl-1,3-oxazolidine. To the dropping funnel is charged 575 g. (6.25 moles) of epichlorohydrin, added dropwise over a period of three hours while the temperature is maintained at 55° C. + 2° C. through the use of controlled air cooling. The mixture is heated at this temperature for 20 hours and is then stripped of unreacted 2-isopropyloxazolidine and excess epichlorohydrin at 65°–70° C./20 mm. Hg. The crude pale yellow product (942 g., 91% yield) thus obtained is wiping-film distilled at 120° C./0.5 mm. Hg to provide 705 g. (75% yield) of clear colorless mobile liquid identified as 3-(3-chloro-2-hydroxypropyl)-2-isopropyl-1,3-oxazolidine.

Analysis for $C_9H_{18}NO_2Cl$: Calculated: %C, 52.10; %H, 8.72; %N, 6.74; %Cl, 17.05. Found: %C, 52.36; %H, 8.60; %N, 6.56; %Cl, 16.75. E. W. ($HClO_4$) Theoret.: 207.87; Found: 205.2. GLC >96% purity.

Step C: 3-(Glycidyl)-2-Isopropyl-1,3-Oxazolidine 3-(3-Chloro-2-hydroxypropyl)-2-isopropyl-1,3-oxazolidine (621 g., 3.0 mole) is charged into a 2-liter, three-necked flask equipped with a mechanical stirrer, thermometer and a dropping funnel. The flask is cooled to 0°–5° C. and 628 g. (2.91 moles) of sodium methoxide (25% solution in methanol) is added dropwise over a period of 3½ hours, the clear solution becoming cloudy upon addition of the first several drops. Stirring is continued for an additional two hours after addition is completed. The solution is allowed to warm to room temperature and the sodium chloride is filtered off. The filtrate is concentrated on an evaporating rotary at 40° C/20 mm. Hg and the residue is refiltered to remove the remaining sodium chloride. The solution is then stripped at 40° C/20 mm. Hg until solvent is no longer removed. The resulting pale yellow liquid weighing 520 g. (98% yield) is wiping-film distilled at 100° C/0.5 mm. Hg to produce 368 g. (71% yield) of 3-(glycidyl)-2-isopropyl-1,3-oxazolidine in the form of a colorless mobile liquid.

Analysis for $C_9H_{17}NO_2$: Calculated: %C, 63.12; %H, 10.00; %N, 8.18. Found: %C, 63.29; %H, 9.68; %N, 7.91. Neutralization Equivalent ($HClO_4$) Calculated: 171.2; Found: 174.6 GLC Analysis 97 + % purity.

EXAMPLE B

The procedure of Step B and then Step C of Example A is carried out on the following substituted 1,3-oxazolidines: (a) 2-butyl-1,3-oxazolidine; (b) 2-methyl-1,3oxazolidine; (c) 2-(n-hexyl)-1,3-oxazolidine; (d) 2-benzyl-1,3-oxazolidine, by the procedure of Step A of Example 1 replacing the isobutyraldehyde with a respective one of the following aldehydes: (a) pentaldehyde; (b) acetaldehyde; (c) n-heptaldehyde; and (d) phenylacetaldehyde.

The products thereby obtained in the successive steps are as follows:

Products of Step B:
Ba. 3-(3-chloro-2 hydroxypropyl)-2-butyl-1,3-oxazolidine;
Bb. 3-(3-chloro-2 hydroxypropyl)-2-methyl-1,3-oxazolidine;
Bc. 3-(3-chloro-2 hydroxypropyl)-2-hexyl-1,3-oxazolidine;
Bd. 3-(3-chloro-2 hydroxypropyl)-2-benzyl-1,3-oxazolidine.

Products of Step C:
Ca. 3-(glycidyl)-2-butyl-1,3-oxazolidine;
Cb. 3-(glycidyl)-2-methyl-1,3-oxazolidine;
Cc. 3-(glycidyl)-2-hexyl-1,3-oxazolidine;
Cd. 3-(glycidyl)-2-benzyl-1,3-oxazolidine.

EXAMPLE 1

Into a three-necked flask (500 ml.) equipped with a mechanical stirrer, thermometer attached to a "thermowatch" and a condenser, there are charged (1) a solution of a polymeric acid obtained by addition-copolymerization of a monomer mixture comprising methyl methacrylate, butyl acrylate and methacrylic acid (MMA/BA/MAA) (relative weight ratio of 20/75/5) and (2) 1.0 equivalent (based on acid content of copolymer) of the epoxide, 3-glycidyl-2-isopropyl-1,3-oxazolidine. The mixture is heated at 85° C. for 5–6 hours whereafter titrimetric data at this time indicated 60–65% conversion of acid to ester. A 50% excess of the same epoxide is then added and the reaction mixture is heated an additional 4–7 hours. The resulting pale yellow solution contains 0.52 meq./g. of amine and 0.625 meq./g. of acid. Eighty percent of the methacrylic acid units in the copolymer have been converted to 3-(3-methacryloxy-2-hydroxypropyl)-2-isopropyl-1,3-oxazolidene units.

EXAMPLES 2 to 5

In a similar manner polymeric oxazolidines are obtained by substituting the appropriate acid copolymer or homopolymer for the "polymeric acid" of Example 1 and following substantially the procedure described therein. The following Table I sets forth the polyacids employed, the appropriate reaction conditions and the amount of product obtained thereby:

TABLE I

| EX. | POLYMERIC ACIDS | TEMP. | HOURS/ SOLVENT | % ACID CONVERSION |
|---|---|---|---|---|
| 2 | BA/MMA/MAA 75 20 5 | 85° C. | 12/No Solvent | 86% |
| 3 | BA/MMA/MAA 75 15 10 | 85° C. | 15/No Solvent | 85% |
| 4 | BA/MMA/MAA 57 35 8 | 85° C. | 15/No Solvent | 90% |
| 5 | MAA* 17.2 g. | 85° C. | 7/Toluene | 70% |

*MAA is a homopolymer of methacrylic acid

EXAMPLES 6, 7, 8

Upon substituting adipic acid, azelaic acid, and isophthalic acid for the "polymeric acid" of the preceding paragraph and following substantially the procedure described therein, there is obtained the corresponding bis-oxazolidine ester products of formula III in which $n$ is 2. Table II sets forth the starting materials employed, the reaction conditions, $R^1$, and the amount of product obtained:

TABLE II

| EX. | ACID | TEMP. | HOUR/ SOLVENT | ACID CONVERSION | —$R^1$— |
|---|---|---|---|---|---|
| 6 | Adipic | 84° C. | 12.5/Aceto-Nitrile | 78% | —$(CH_2)_4$— |
| 7 | Azelaic | 80° C. | 12.0/Toluene | 79% | —$(CH_2)_7$— |

TABLE II-continued

| EX. | ACID | TEMP. | HOUR/ SOLVENT | ACID CONVERSION | —R'— |
|---|---|---|---|---|---|
| 8 | Isophthalic | 80° C. | 11.5/Toluene | 80% | 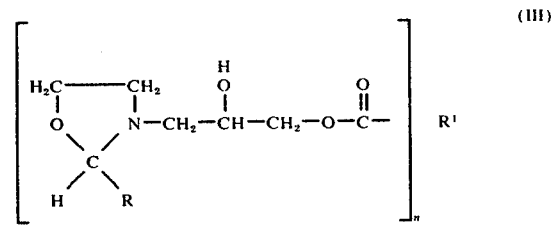 |

EXAMPLE 9

An acid-terminated polyester of ethylene glycol-/adipic acid (47.0 g., 70 meq.) having a molecular weight of about 1400 and 3-glycidyl-2-isopropyl-1,3-oxazolidine (11.98 g., 70 meq.) are charged into a 100 ml., three-neck flask equipped with a mechanical stirrer, condenser with a drying tube and a thermometer. The polyester is a hard, white solid which melts at 40°–50° C. and has an acid number of 84.15 (1.49 meq/g.). The mixture is heated at 70° C. for 9 hours to produce a product in which 65–70% of initially charged acid is consumed. An additional 6 g. (35 meq.) of 3-glycidyl-2-isopropyl-1,3-oxazolidine is charged and heating at 70° C. is continued for about 4 hours to yield a product in which 78% of the initially charged acid is converted to an ester.

EXAMPLE 10

A coating composition is prepared by mixing a solution in toluene containing 20% by weight of the product of Example 9 and 15% by weight of the 2-isocyanatoethyl-6-isocyanatocaproate. The solution is sprayed on panels of wood, aluminum and steel primed with an alkyd/melamineformaldehyde coating. The curing is effected at ambient temperature and relative humidity (17° C. and 40%). A clear hard film is obtained in about 3 hours.

The polyester condensation product may also be any of the common acid-terminated alkyd resins having an acid number from 5 to 90, preferably at least 20, including oil-modified alkyd resins. For example, simple alkyds that may be used may be those obtained by condensing a polycarboxylic acid, such as o-phthalic, terephthalic, isophthalic, pyromellitic, succinic, glutaric, adipic, or sebacic acids, with a polyol or polyhydric alcohol such as ethylene glycol, diethylene glycol, glycerol, pentaerythritol, sorbitol, inositol, trimethylolethane ($H_3CC(CH_2OH)_3$)tetramethylolcyclohexanol, di- and polypentaerythritol. Besides the dicarboxylic acids mentioned, the acid component may also contain an acid having 3 or more carboxylic groups, such as trimesic acid. The polyol employed is ordinarily an aliphatic compound formed of C, H, and O atoms in which there are from 2 to 10 carbon atoms and 2 to 6 hydroxyl groups. The polyhydric alcohol component from which the alkyd is derived may comprise up to 25% by weight of at least one alcohol containing at least three hydroxyl groups. If desired, there may be used as a part of the dicarboxylic acid component one or more ethylenically unsaturated acids, such as maleic acid, fumaric acid, or the polycarboxylic acid compounds obtained by interacting maleic anhydride with abietic acid, ricinoleic or eleostearic acids. The unsaturated dicarboxylic acid may amount to fifty percent of the total dicarboxylic acid used, but is preferably not over 25% of such total.

The alkyds may be modified with a higher monobasic aliphatic acid having 12 to 30 carbon atoms, such as a fatty acid or fatty acid mixture derived from drying, semi-drying, or nondrying oils or fats in which the fatty acid has from 12 to 30 carbon atoms and up. The modifying fatty acid may be lauric acid, myristic acid, coconut oil fatty acids, palm oil fatty acids, palmitic acid, oleic acid, stearic acid, linolenic acid, or fatty acids obtained by hydrogenation of fish, animal, or vegetable oils or fats.

Moisture-curable compositions useful in coating compositions and for impregnation, e.g., of leather, are prepared by mixing the oxazolidine derivatives of the present invention, especially those of formula III in which $R^1$ is the residue of a condensation polymer, as in Examples 9 and 10, or of an addition polymer, as in Examples 2 to 5, with a polyisocyanate or a prepolymer of a polyisocyanate. Thus, the oxazolidines of the present invention can, with advantage, be used in the hydrocurable systems described and claimed in Emmons U.S. Pat. No. 3,743,626.

It is to be understood that changes and variations may be made without departing from the spirit and scope of the invention as defined in the appended claims.

We claim:

1. A compound of the formula:

$$\left[ \begin{array}{c} H_2C\text{------}CH_2 \\ | \quad\quad | \\ O \quad\quad N\text{---}CH_2\text{---}\overset{H}{\underset{|}{C}}\text{---}CH_2\text{---}O\text{---}\overset{O}{\underset{\|}{C}}\text{---} \\ \diagdown\,\diagup \\ C \\ \diagup\,\diagdown \\ H \quad\quad R \end{array} \right]_n R^1 \quad\quad (III)$$

wherein,

R is a member selected from hydrogen, alkyl having 1 to 8 carbon atoms, and benzyl n is an integer having a value of 1, 2, or more, $R^1$, when n is 1, is phenyl, benzyl, or alkyl or alkenyl of 2 to 10 carbon atoms, $R^1$, when n is 2, is a covalent bond, an alkylene chain of 2 to 10 carbon atoms, an alkenylene chain of 2 to 10 carbon atoms, or phenylene, and $R^1$, when n is more than 2, is a residue of a polycarboxylic acid selected from the group consisting of aconitic, trimesic, tricarballylic and citric acids.

2. The compound of claim 1 wherein n is 1 and $R^1$ is alkenyl having 2 to 8 carbon atoms.

3. The compound of claim 1 wherein R is hydrogen, n is 1, and $R^1$ is alkenyl having 2 to 8 carbon atoms.

4. A compound according to claim 1 wherein R is alkyl having 2–10 carbon atoms and $R^1$ is an alkenyl group selected from $H_2C = CH$— and $H_2C = C(CH_3)$—.

5. The compound of claim 1 wherein R is isopropyl, $n$ is 1, and $R^1$ is vinyl or alpha-methylvinyl.

6. The compound of claim 5 wherein $R^1$ is vinyl.

7. The compound of claim 1 wherein R is alkyl having 2–10 carbon atoms, $n$ is 2, and $R^1$ is an alkylene chain of 2–10 carbon atoms.

8. The compound of claim 1 wherein R is isopropyl, $n$ is 2, and $R^1$ is an alkylene chain of 2–10 carbon atoms.

9. The compound of claim 1 wherein R is isopropyl, $n$ is 2, and $R^1$ is selected from the group consisting of butylene, heptylene, and phenylene.

10. The compound of claim 9 wherein $R^1$ is butylene.

11. The compound of claim 9 wherein $R^1$ is phenylene.

12. The compound of claim 9 wherein $R^1$ is heptylene.

* * * * *

UNITED STATES PATENT AND TRADEMARK OFFICE
CERTIFICATE OF CORRECTION

PATENT NO. : 4,002,637
DATED : January 11, 1977
INVENTOR(S) : Sheldon N. Lewis et al.

It is certified that error appears in the above-identified patent and that said Letters Patent are hereby corrected as shown below:

Column 2, line 62 insert --to-- after "(I)"

Column 3, line 34 "completion" should be --competition--.

Column 6, line 58 "%CC" should be --%C--.

Column 7, line 13 "207.87" should be --207.7--.

Signed and Sealed this

Twenty-ninth Day of March 1977

[SEAL]

Attest:

RUTH C. MASON
Attesting Officer

C. MARSHALL DANN
Commissioner of Patents and Trademarks